(12) United States Patent
Kim

(10) Patent No.: US 6,245,320 B1
(45) Date of Patent: Jun. 12, 2001

(54) INHIBITION OF MUCIN RELEASE FROM AIRWAY GOBLET CELLS BY POLYCATIONIC PEPTIDES

(75) Inventor: Kwang Chul Kim, Ellicott City, MD (US)

(73) Assignee: University of Maryland, Baltimore, MD (US)

( * ) Notice: Subject to any disclaimer, the term of this patent is extended or adjusted under 35 U.S.C. 154(b) by 0 days.

(21) Appl. No.: 09/387,501

(22) Filed: Sep. 1, 1999

(51) Int. Cl.[7] .............................. A61K 9/72; A61K 38/03; A61K 38/08; A61K 38/10; A61K 38/16

(52) U.S. Cl. .............................. 424/43; 424/45; 424/400; 514/2; 514/12; 514/13; 514/14; 514/15; 514/16; 514/17

(58) Field of Search .................................. 424/43, 44, 45, 424/46, 400; 514/2, 12, 13, 14, 15, 16, 17, 21; 530/300, 324, 325, 326, 327, 328, 329, 330; 930/290

(56) References Cited

U.S. PATENT DOCUMENTS

| 4,939,169 | * | 7/1990 | Bundy et al. ......................... 514/459 |
| 5,716,931 | * | 2/1998 | Vedia et al. ............................ 514/12 |
| 5,767,068 | * | 6/1998 | Van Devanter et al. ................ 514/9 |
| 5,948,681 | * | 9/1999 | Scanlin et al. ....................... 435/455 |
| 6,057,291 | * | 5/2000 | Hancock et al. ....................... 514/12 |

FOREIGN PATENT DOCUMENTS 8-319208 * 12/1996 (JP) .

OTHER PUBLICATIONS

Goodman and Gilman (1985), The Pharmacological Basis for Therapeutics, pp. 955–956.

Kim et al., "$P_x$ purinoceptor regulation of mucin release by airway goblet cells in primary culture", Br. J. Pharmacol. (1991), Vo. 103, pp. 1053–1056.

Kim et al., "Human neutrophil elastase releases cells surface mucins from primary cultures of hamster tracheal epithelial cells", Proc. Natl. Acad. Sci, USA, vol. 84, pp. 9304–9308, Dec. 1987.

Kim et al., "Biochemical Characterization of mucous Glycoproteins Synthesized and Secreted by Hamster Tracheal Epithelial Cells in Primary Culture", The J. of Biol. Chem., vol. 260, No. 7, Apr. 10, 1985, pp. 4021–4027.

Kim et al., "Mechanisms of Airway Goblet Cell Mucin Release: Studies with Cultured Tracheal Surface Epithelial Cells", Am. J. of Respiratory Cell Mol. Biol., vol. 1, 1989, pp. 137–143.

Kim et al., "Secretions from Primary Hamster Tracheal Surface Epithelial Cells in culture: Mucin–Like Glycoproteins, Proteoglycans, and Lipids", Experimental Lung Research, vol. 15, pp. 299–314, (1989).

(List continued on next page.)

Primary Examiner—Jeffrey E. Russel
(74) Attorney, Agent, or Firm—Millen White Zelano & Branigan

(57) ABSTRACT

Polycationic peptides have been shown to be effective inhibitors of mucin secretion. Inhibition of mucin secretion using these polycationic peptides may be an important tool in the treatment of diseases associated with mucin hypersecretion, including asthma, chronic bronchitis, cystic fibrosis, and bronchiectasis.

22 Claims, 13 Drawing Sheets

OTHER PUBLICATIONS

Adler et al., "Oxygen Metabolites Stiumlate Release of High–Molecular–Weight Glycoconjugates by Cell and Organ Cultures of Rodent Respiratory Epithelium via an Arachiodonic Acid–dependent Mechanism", J. Clin, Invest., vol. 85, Jan. 1990, pp. 75–85.

Fahy et al., "Markers of Mucus Secretion and DNA Levels in Induced Sputum from Asthmatic and from Healthy Subjects", Am Rev. Respir Dis., vol. 147, pp. 1132–1137, 1993.

Temann et al., "A Novel Role for Murine IL–4 In Vivo: Induction of MUC5AC Gene Expression and Mucin Hypersecretion", Am. J. Respir, Cell Mol. Biol., vol. 16, pp. 471–478, 1997.

Adler et al., "Platelet–activating Factor Provokes Release of Mucin–like Glycoproteins from Guinea Pig respiratory Epithelial Cells via a Lipoxygenase–dependent Mechanism", Am. J. Respir. Cell Mol. Biol., vol. 6, pp. 550–556, 1992.

Roberts et al. Basic Principles Of Organic Chemistry, 2nd. ed. Menlo Park: W.A. Benjamin, Inc. pp. 1101, 1209, 1210, 1977.*

Hayashi et al. The structure of PA48009...J. Nitibiotics, vol. 43, No. 11, pp. 1421–1430, Nov. 1990.*

The Merck Index, $11^{th}$ ed. Rahway: Merck & Co., Inc. p. 1038, 1989.*

* cited by examiner

INHIBITION OF MUCIN RELEASE FROM AIRWAY GOBLET CELLS BY POLYCATIONIC PEPTIDES

BACKGROUND OF THE INVENTION

Hypersecretion of mucin in the airways is associated with a variety of diseases, including asthma, chronic bronchitis, cystic fibrosis, and bronchiectasis. Effective measures for inhibiting mucin secretion in the airways would be useful to mitigate the deleterious effects associated with mucin hypersecretion. Effective inhibition of mucin secretion would also be useful in enhancing the delivery of therapeutic agents to the airways and via the airways.

SUMMARY OF THE INVENTION

It has been discovered, according to this invention, that polycationic peptides inhibit mucin secretion from airway goblet cells. It has also been discovered that the inhibition of mucin secretion by polycationic peptides is accompanied by minimal cytotoxicity to cells of airways, thereby by indicating the suitability of polycationic peptides for use in animals, particularly humans, for the inhibition of mucin secretion. It has also been discovered that polycationic peptides can prevent $SO_2$ induced goblet cell metaplasia.

It is contemplated as part of this invention that polycationic molecules, particularly polycationic peptides or peptide mimetics, may be employed to inhibit mucin secretion for a variety of therapeutic purposes. For example, the polycationic molecules may be administered to alleviate mucin hypersecretion, particularly in disease conditions associated with mucin hypersecretion. For example, the compositions of the invention may be administered to treat asthma, chronic bronchitis, cystic fibrosis, bronchiectasis, and chronic obstructive pulmonary disease. As another example, the polycationic molecules may be administered to reduce mucin in the airways in order to facilitate the bioavailability of therapeutic agents targeted to the airways, such as, for example, bronchodialators. As another example, the polycationic molecules may be administered to reduce mucin in the airways, thereby minimizing airway impedance and facilitating therapeutic agent delivery to the alveoli or through the alveoli to the blood stream.

Treat, treated or treatment, as used herein, means the administration of polycationic molecules to the airways of an animal to prevent, mitigate, alleviate or cure a disease or the symptoms of a disease.

Animal, as used herein, means any vertebrate animal, including humans, farm animals and pets.

Airways or airway, as used herein, refers to any part of the lungs that is capable of mucin production.

Polycationic molecules that may be used in accordance with this invention include, but are not limited to, polycationic peptides and polycationic peptide mimetics. Polycationic peptides are a preferred polycationic molecule because they can be easily degraded to amino acids.

The polycationic peptides typically comprise about 5 to about 60 amino acids, preferably about 5 to about 40 amino acids, and more preferably about 10 to about 25 amino acids. Smaller molecules are preferred because of greater ease of handling. A polycationic peptide typically possesses a sufficient number of positively charged amino acids such that the pKa of the peptide is greater than 9.0, preferably greater than 10.0, and more preferably greater than 11.0. Typically, at least about 20% of the amino acid residues are positively charged, preferably at least about 40%, more preferably at least about 60%, and most preferably at least about 80%. Positively charged amino acids include, for example, lysine, arginine, or ornithine. Positively charged refers to the side chains of the amino acids which have a net positive charge at a pH 7.0. The effectiveness of any particular polycationic molecule in inhibiting mucin, with minimal toxicity, may be established, for example, using techniques and models described herein. At an optimal concentration, a polycationic molecule, polycationic peptide, or polycationic peptide mimetic, according to this invention, preferably inhibits mucin secretion at least about 50%, more preferably at least about 70%, and most preferably at least about 90%. The degree of inhibition of mucin secretion may be determined, for example, using a hamster tracheal surface epithelial (HTSE) cell culture system as described in the Examples herein. The degree of inhibition of mucin secretion may also be determined using other techniques, including in vitro techniques such as are described, for example, in Adler et al., 1990, *J. Clin. Invest.* 85:75–85 and in Adler et al., 1992, *Am. J. Respir. Cell Mol. Biol.* 6:550–556 and including in vivo techniques such as are described, for example, in Temann et al., 1997, *Am. J. Respir. Cell Mol. Biol.* 16:471–478 and Fahy et al., 1993, *Am. Rev. Respir. Dis.* 147:1132–1137. A polycationic molecule, polycationic peptide, or polycationic peptide mimetic according to this invention preferably has minimal cytotoxicity. Cytotoxicity may be determined, for example, using an LDH release assay, a $^{51}Cr$ release assay, or a cell exfoliation assay as described in the examples. Cytotoxicity may also be determined, for example, using an HTSE cell culture system as described in the examples. In determining cytotoxicity for polycationic molecules of the invention using the above listed assays, LDH release, $^{51}Cr$ release, or cell exfoliation is typically less than about 115% of that observed in control cells, preferably less than about 110%, and more preferably less than about 105%.

Preferred polycationic peptides for use in accordance with this invention are poly-L-lysine, poly-L-arginine, or poly-L-lysine and poly-L-arginine heteropolymers. Polycationic peptides containing other positively charged amino acid residues such as, for example, poly-L-ornithine, may also be employed. The amino acids of the polycationic peptides may be naturally occurring proteogenic amino acids as well as non-naturally occurring amino acids such as amino acid analogs. One of skill in the art would know that this definition includes, unless otherwise indicated, naturally occurring proteogenic (D) or (L) amino acids, chemically modified amino acids, including amino acid analogs such as penicillamine (3-mercapto-D-valine), naturally occurring non-proteogenic amino acids such as norleucine and chemically synthesized compounds that have properties known in the art to be characteristic of an amino acid. As used herein, the term "proteogenic" indicates that the amino acid can be incorporated into a protein in a cell through well-known metabolic pathways. The choice of including an (L)- or a (D)-amino acid into a peptide of the present invention depends, in part, on the desired characteristics of the peptide. For example, the incorporation of one or more (D)-amino acids can confer increasing stability on the peptide in vitro or in vivo. As used herein, the term "amino acid equivalent" refers to compounds which depart from the structure of the naturally occurring amino acids, but which have substantially the structure of an amino acid, such that they can be substituted within a peptide which retains biological activity. Thus, for example, amino acid equivalents can include amino acids having side chain modifications or substitutions, and also include related organic acids, amides or the like. The term "amino acid" is intended to include amino acid equivalents. The term "residues" refers both to amino acids and amino acid equivalents.

As used herein, the term "peptide" is used in its broadest sense to refer to compounds containing amino acid equivalents or other non-amino groups, while still retaining the desired functional activity of inhibiting mucin secretion. Peptide equivalents can differ from conventional peptides by, for example, the replacement of one or more amino acids with related organic acids (such as PABA) or the substitution or modification of side chains or functional groups. It is to be understood that limited modifications can be made to a peptide without destroying its biological function, such as for example, the addition of chemical moieties such as amino or acetyl groups.

Polycationic peptides that may be used in accordance with this invention include naturally occurring peptides, synthetic peptides, and analogs thereof. The effectiveness of any particular polycationic peptide in inhibiting mucin secretion can be established, for example, by using the techniques described herein.

Polycationic peptides useful for this invention may be produced using techniques that are well known in the art, including chemical synthesis techniques and recombinant DNA techniques. The production of polycationic peptides using recombinant DNA techniques is described, for example, in U.S. Pat. No. 5,593,866. Chemical synthesis of peptides can be accomplished using techniques that are well known in the art, such as TBOC or FMOC protection of alpha-amino groups. (See, Coligan, et al., *Current Protocols in Immunology*, Wiley Interscience, 1991, Unit 9). Peptides of the invention can also be synthesized by the well known solid phase peptide synthesis methods (Merrifield, *J. Am. Chem. Soc.*, 85:2149 (1962); Stewart and Young, *Solid Phase Peptide Synthesis* (Freeman, San Francisco, 1969) pp. 27–62).

Non-peptide compounds that mimic the mucin inhibiting function of polycationic peptides, peptide mimetics, can also be employed in conjunction with the invention. Such peptide mimetics can be produced as described, for example, by Saragovi et al., *Science* 253:792–95 (1991). Peptide mimetics are molecules which mimic elements of protein secondary structure. See, for example, Johnson et al., Peptide Turn Mimetics, in *Biotechnology and Pharmacy*, Pezzuto et al., Eds., (Chapman and Hall, New York 1993). The underlying rationale behind the use of peptide mimetics is that the peptide backbone of proteins exists chiefly to orient amino acid side chains in such a way as to facilitate molecular interactions. For the purposes of the present invention, appropriate peptide mimetics are considered to be the equivalent of mucin inhibiting polycationic peptides.

If the compounds described above are employed, the skilled artisan can routinely ensure that such compounds are amenable for use with the present invention in view of the mucin inhibition assays and cell toxicity assays described herein.

It is also contemplated as part of the invention that low molecular weight polyanions such as, for example, low molecular weight heparin may be employed to modulate the effect of the polycationic molecules in inhibiting mucin release, or to mitigate cytotoxcity of the polycationic peptides.

The invention also includes various pharmaceutical compositions and pharmaceutical articles of manufacture that may be employed to inhibit mucin secretion in the airways of an animal. The pharmaceutical compositions according to the invention are prepared by bringing a polycationic molecule into a form suitable for administration to a subject using adjuvants, carriers, excipients and additives or auxiliaries, or devices. Pharmaceutically acceptable adjuvants, carriers, excipients, additives or auxiliaries are described, for example, in *Remington's Pharmaceutical Sciences*, 15th ed. Easton: Mack Publishing Co. (1990), the contents of which are hereby incorporated by reference. The pH and exact concentration of the various components of the pharmaceutical composition are adjusted according to routine skills in the art. See *Goodman and Gilman's The Pharmacological Basis for Therapeutics* (7 th ed.). Particularly preferred adjuvants for use in conjunction with the invention are inhalant adjuvants. An inhalant adjuvant, as used herein, refers to any composition which facilitates the airborne administration of the polycationic molecules to the airways of an animal.

The polycationic peptides may be administered to the airways in any number of ways that are well known in the art, including via inhalation or via physical application, including the use of a bronchoscope. A preferred method for administration is by inhalation, including for example, both oral inhalation and nasal inhalation. For inhalation, the compounds of the invention are conveniently delivered from an insufflator, a nebulizer, a pump, a pressurized pack, or other convenient means of delivering an aerosol or non-aerosol spray of a powder or a liquid. Pressurized packs may comprise a suitable propellant such a liquefied gas or a compressed gas. Liquefied gases include, for example, fluorinated chlorinated hydrocarbons, hydrochlorofluorocarbons, hydrochlorocarbons, hydrocarbons, and hydrocarbon ethers. Compressed gases include, for example, nitrogen, nitrous oxide, and carbon dioxide. In particular, the use of dichlorodifluoromethane, trichlorofluoromethane, dichlorotetrafluoroethane, carbon dioxide or other suitable gas is contemplated. In the case of a pressurized aerosol, the dosage unit may be determined by providing a valve to deliver a metered amount. Alternatively, for administration by inhalation or insufflation, the compounds of the invention may be in the form of a dry powder composition, for example, a powder mix of the compound and a suitable powder base such as lactose or starch. The powder composition may be presented in unit dosage form such as, for example, capsules, cartridges, or blister packs from which the powder may be administered with the aid of an inhalator or insufflator.

In accordance with the invention, the compounds of the invention may be administered to inhibit mucin secretion in conjunction with other therapeutic agents. For example, for the treatment of asthma, polycationic polypeptides may be administered in conjunction with sympathomimetic bronchodilators, anticholinergic bronchodilators, theophylline bronchodialators, corticosteroids, and antimediators.

It will be appreciated that the amount of the polycationic molecule or the polycationic peptide to be administered in conjunction with the invention will vary depending upon the condition and the animal being treated. Suitable dosage amounts can be routinely determined by one of ordinary skill in the art. The desired daily dose may be presented in single dose or as divided doses administered at appropriate intervals, such as two, three, four or more sub-doses per day.

BRIEF DESCRIPTION OF THE FIGURES

FIG. 1 is a bar graph showing the effects of poly-L-arginine (PLA) poly-L-lysine (PLL) on mucin release in HTSE cells. Confluent cells in 16 mm wells were metabolically radiolabeled with $^3$H-glucosamine for 24 hr and chased for 30 min in the presence of varying concentrations of either PLA or PLL. The amount of $^3$H-mucins in the spent medium was measured. Each bar represents a mean±S.E.M from four culture wells. An (*) indicates a value which is significantly different ( $p<0.05$) from a control value, based on the Student's t-test for unpaired samples.

FIG. 2 is a bar graph showing the effects of PLA and PLL on LDH release from HTSE cells. Confluent cells in 16 mm wells were treated with varying concentrations of either PLA or PLL for 30 min, and aliquots of the spent media were collected and assayed for LDH levels. Each bar represents a mean±S.E.M from four culture wells. There was no significant difference ($p>0.05$) among different concentration groups, based on the Student's t-test for unpaired samples.

FIG. 3 is a bar graph showing the effects of low molecular weight heparin (LMWH) in inhibiting the inhibitory effect of polycationic peptides on mucin release in HTSE cells. Confluent cells in 16 mm wells were metabolically radio-labeled with $^3$H-glucosamine for 24 hrs and pretreated with $2 \times 10^{-5}$ M LMWH for 5 min prior to chasing for 30 min in the presence of either $10^{-5}$ M PLA or $10^{-5}$ M PLL. The amount of $^3$H-mucins in the spent medium was measured. Each bar represents a mean ±S.E.M. from four culture wells. A (P) represents polycationic peptides and an (H) represents low molecular weight heparin. An (*) indicates a value that is significantly different ($p<0.05$) from a control value based on the Student's t-test for unpaired samples.

FIG. 4 is a graph indicating the results of CM-sepharose cation-exchange chromatography of polycationic peptides following N-acetylation. A solution of PLA at a concentration of $10^{-4}$ M was N-acetylated using acetic anhydride, and the acetylated and the original (unacetylated) forms of PLA were separated by CM-Sepharose cation-exchange chromatography. The unacetylated PLA was retained on the column (Panel A) and the N-acetylated PLA was eluted from the column (Panel B). The yield of N-acetylated PLA was greater than 95%.

FIG. 5 is a bar graph showing the effects of N-acetylated PLA and N-acetylated PLL on mucin release by HTSE cells. Confluent cells in 16 mm wells were metabolically radio-labeled with $^3$H-glucosamine for 24 hr and chased for 30 min in the presence of $10^{-5}$ M of polycationic peptides. The amount of $^3$H-mucins in the spent medium was measured. P: original formulations of the unacetylated polycationic peptides, without column purification. N-AcP: N-acetylated polycationic peptides (column purified). P-P: unacetylated polycationic peptides that were column purified. Each bar represents a mean±S.E.M. from four culture wells. An asterisk (*) indicates a value that is significantly different ($p<0.05$) from the control value based on the Student's t-test for unpaired samples.

FIG. 6 is a bar graph showing the effect of polycationic peptides on ATP-induced mucin release in HTSE cells. Confluent cells in 16 mm wells were metabolically radio-labeled with $^3$H-glucosamine for 24 hr and chased for 30 min in the presence of a combination of ATP, at a concentration of $2 \times 10^{-4}$ M, and polycationic peptides, at a concentration of $10^{-5}$ M. The amount of $^3$H-mucins in the spent medium was measured. Each bar represents a mean±S.E.M. from four culture wells. ATP is indicated as (A). An asterisk (*) indicates a value that is significantly different ($p<0.05$) from the control value based on the Student's t-test for unpaired samples.

Figure 13:
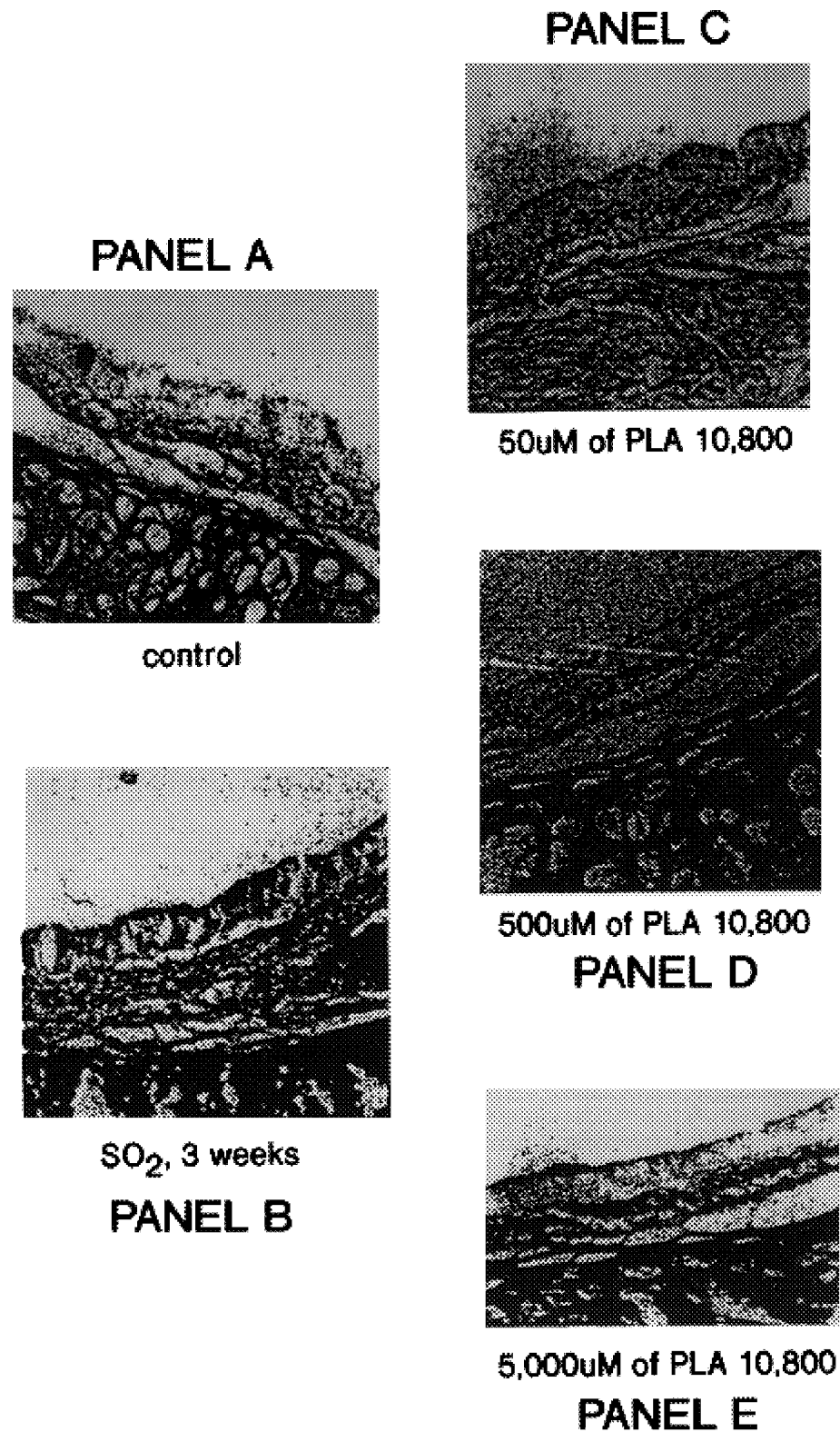

FIG. 13, Panels A-E are images of rat lung tissue sections showing the effects of PLA on $SO_2$ induced metaplasia in rat. Panels A-E show lung tissue from animals that were treated as follows: (A) control untreated animals; (B) animals treated with $SO_2$; (C) animals treated with both $SO_2$ and 50 $\mu$M PLA (MW 10,800); (D) animals treated with both $SO_2$ and 500 $\mu$M PLA (MW 10,800); (E) animals treated with both $SO_2$ and 5,000 $\mu$M of PLA (MW 10,800).

Without further elaboration, it is believed that one skilled in the art can use the preceding description to utilize the present invention to its fullest extent. Therefore, the following preferred specific embodiments illustrate but do not limit the remainder of the disclosure in any respect.

EXAMPLES

In the following examples, all parts and percentages are by weight unless otherwise indicated.

Example 1

Effects of PLA and PLL on Mucin Release from Airway Goblet Cells.

The effects of poly-L-arginine (PLA) and poly-L-lysine (PLL) on mucin release from cultured airway goblet cells were evaluated. Tracheas obtained from 7–8 week old male Golden Syrian hamsters (Harlan Sprague Dawley, Indianapolis, Ind.) were used to establish a hamster tracheal surface epithelial (HTSE) cell culture. HTSE cells were harvested and cultured on a thick collagen gel as described in Kim et al., 1989, *Exp. Lung Res.* 15: 299–314. Mucins were metabolically radiolabeled by incubating confluent cultures (24 well plate, $5 \times 10^5$ cells/well) with 0.2 ml/well of a "complete" medium containing 10 $\mu$Ci/ml of $^3$H-glucosamine for 24 hours as described in Kim et al., 1989, *Am. J Resp. Cell Mol. Biol.* 1: 137–143. The "complete" medium was prepared by supplementing a mixture of Medium 199/Dulbecco's modified Eagle's medium (DME) (1:1) with insulin (5 $\mu$g/ml), transferrin (5 $\mu$g/ml), epidermal growth factor (12.5 ng/ml), 0.1 $\mu$M hydrocortisone, 0.01 $\mu$M sodium selenite, 0. 1 $\mu$M retinoic acid, and 5% fetal bovine serum (Hyclone, Logan, Utah). At the end of the 24 hour incubation period, the spent media (the pretreatment sample) were collected, and the labeled cultures were washed twice with Dulbecco's PBS without $Ca^{++}$ and $Mg^{++}$ and then chased for 30 min in the presence of varying concentrations of poly-L-arginine (PLA, average MW 8,900) or poly-L-lysine (PLL, average MW 9,600). The chased media are referred to as the treatment samples. PLA and PLL were prepared in phosphate buffered saline (PBS), and the final pH's of these solutions were adjusted to be between 7.0 and 7.4. PBS solutions within this pH range do not affect mucin release from HTSE cells; Kim et al.,1989, *Am. J. Resp. Cell Mol. Biol.* 1: 137–143. At the end of the chase period, floating cells and cell debris were removed from the treatment samples by centrifugation at 12,000 ×g for 5 min. Fifty μl of the treatment samples were used for lactate dehydrogenase (LDH) assay (as discussed in Example 2 below) and the remaining samples were stored at −80° C. until assayed for their $^3$H-mucin contents. High molecular weight glycoconjugates that were excluded after Sepharose CL-4B (Pharmacia, Upsaala, Sweden) gel-filtration column chromatography and that were resistant to hyaluronidase, were defined as mucins, as described in Kim et al., 1985, *J. Biol. Chem.* 260:4021:4027. Mucins were measured by column chromatography as described in Kim et al, 1987, *Proc. Natl. Acad. Sci. USA* 84:9304–9308.

Figure 1:
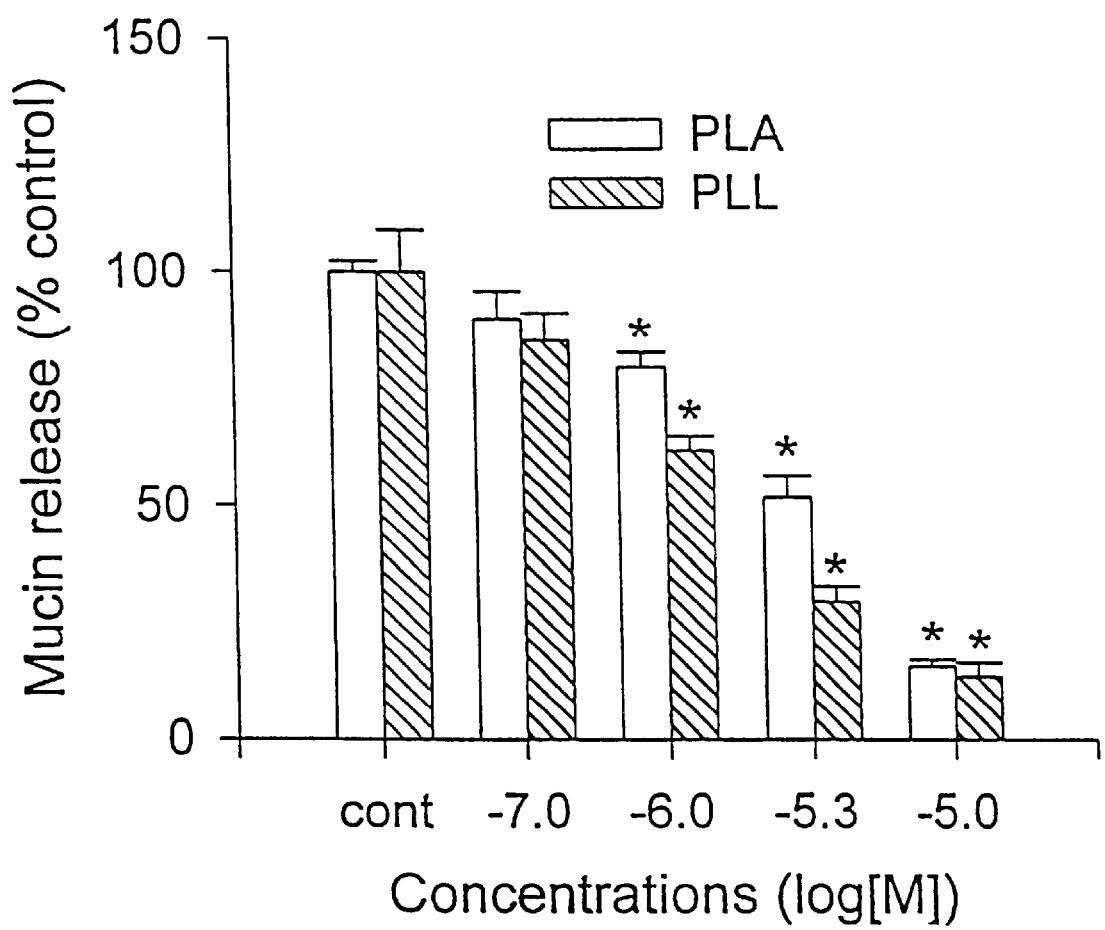

As shown in FIG. 1, both PLA and PLL caused a dose-dependent decrease in the amount of mucins present in the spent media of the HTSE cell cultures, indicating the inhibition of mucin release by these polycationic peptides. Treatment of HTSE cells with varying concentrations of PLA resulted in a dose-dependent decrease in the amount of released mucins, reaching an 85% "inhibition" at $10^{-5}$ M (FIG. 1). PLL showed a similar pattern of effect with an 87% "inhibition" at $10^{-5}$ M (FIG. 1). The decrease in mucin production was not attributable to degradation of mucins during the treatment period or to interference with the mucin assay (gel-filtration column chromatography) by the polycationic peptides. These possibilities were examined using purified $^3$H-mucins that had been prepared as described in Kim et al., 1985, *J. Biol. Chem.* 260:4021:4027. The pH of the medium was not a contributing factor to the decrease in mucin production since PLA and PLL were prepared as $10^{-4}$ M solutions in PBS, with a pH of 7.4. Mucin release from HTSE cells is not affected by this pH (Kim et al., 1989, *Am. J. Resp. Cell Mol. Biol.* 1: 137–143).

Example 2

Effects of PLA and PLL on LDH release, $^{51}$Cr Release, and Cell Exfoliation.

The effects of PLA or PLL on cell toxicity were also examined. The possible cytotoxicity of these polypeptides was assessed by four different methods: (a) LDH release, (b) $^{51}$Cr release, (c) cell exfoliation, and (d) light microscopy. Cultures were treated with either PLA or PLL for 30 min, and then assayed as follows. An LDH assay was conducted using an LDH assay kit (LD-L 10) (Sigma Chemical Co., St. Louis, Mo.), according to the manufacturer's directions. A $^{51}$Cr release assay was carried out as described in Kim et al., 1987, *Proc. Natl. Acad Sci. USA* 84:9304–9308. The degree of exfoliation was measured by counting the floating cells at the end of the 24 hr post-treatment period. Floating cells were collected as a pellet from spent media by centrifugation at 200 ×g for 5 min at 4° C. The resulting cell pellet was suspended in a solution containing 0.05% Trypsin and 0.02% EDTA, and the suspension was incubated at 37° C. for 10 min before dissociated cells were counted using a hemacytometer.

Figure 2:
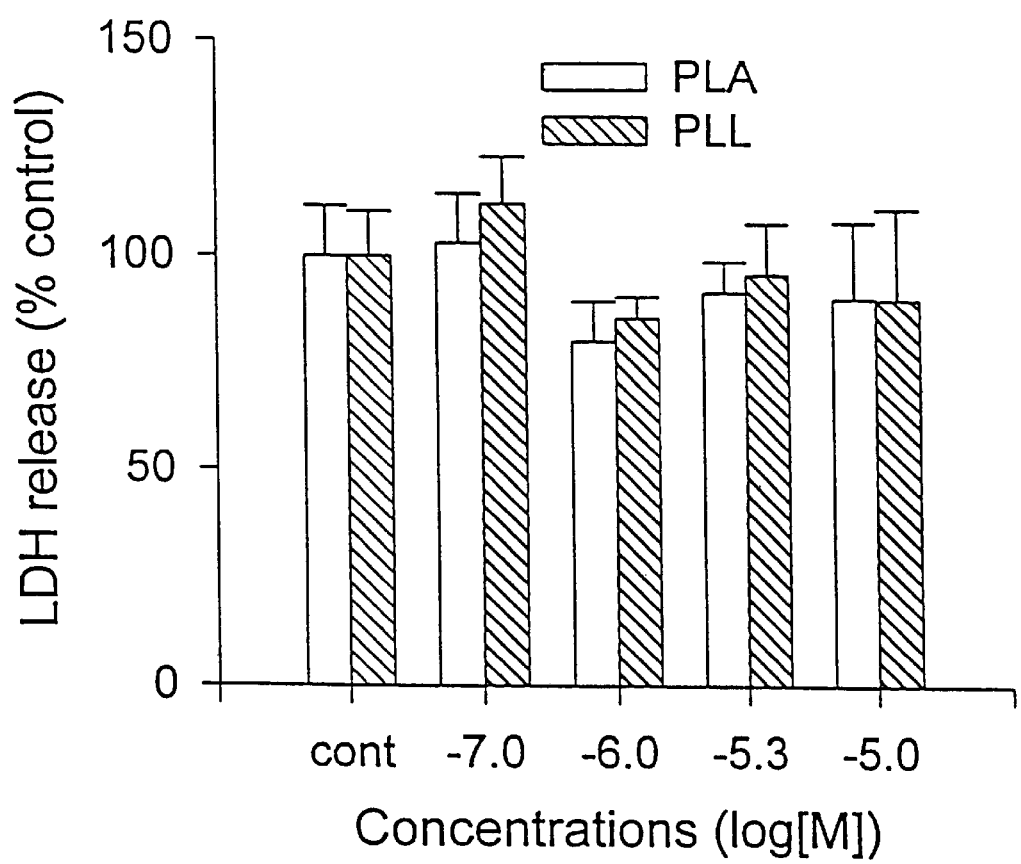

There was no significant difference between the control and the treated groups in any of the cytotoxicity assessments. As shown in FIG. 2, treatment of HTSE cells with either $10^{-5}$ M PLA or $10^{-5}$ M PLL for 30 min caused no significant increases in LDH release. Additionally, the same concentration of PLA or PLL caused no significant change in $^{51}$Cr release from HTSE cells: 100±4% for control, 102±11% for PLA, and 103±10% for PLL. The number of floating cells/well during the 24 hr post-treatment period was also not significantly different among the control and treated groups: 1992±132 for control, 2154±184 for cells treated with $10^{-5}$ M PLA, and 1920±70 for cells treated with $10^{-5}$ M PLL. There was no apparent microscopic difference, using light microscopy, between control and treated HTSE cells, either at the end of the 30 min treatment period or at the end of the 24 hr post-treatment period. Therefore, in primary HTSE cells, both PLA and PLL do not appear to be toxic at the concentrations that showed an inhibitory effect on mucin production.

Example 3

Determination of Whether the Inhibitory Effects of Polycationic Peptides on Mucin Production is Due to the Positive Charges on the Peptides.

An examination of whether the inhibitory effects of polycationic peptides on mucin production is due to the positive charges on the peptides was conducted using both pharmacological and chemical approaches. In one experiment, low molecular weight heparin (LMWH), a highly negatively charged polysacharride, was added to neutralize the polycationic peptides. In a second experiment, the polycationic peptides were N-acetylated to block the positive charges.

Figure 3:
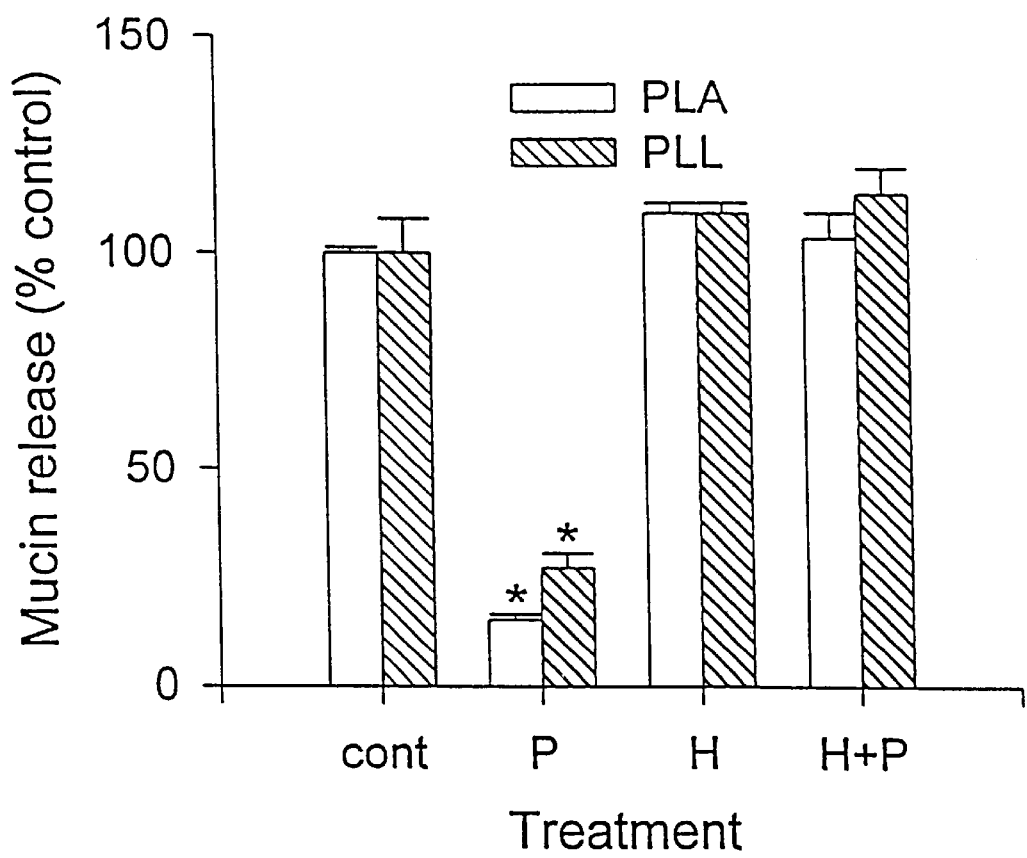

In the first experiment, low molecular weight heparin (LMWH), derived from porcine intestinal mucosa and having an average MW of 6,000, was prepared as a solution in PBS, with a final pH of between 7.0 and 7.4. The LMWH was added to the cell cultures 5 min prior to the addition of the polycationic peptides. As shown in FIG. 3, the inhibitory effect by either $10^{-5}$ M PLA or $10^{-5}$ M PLL on mucin release was completely blocked by pretreatment of HTSE cells with $2 \times 10^{-5}$ M LMWH.

Figure 4:
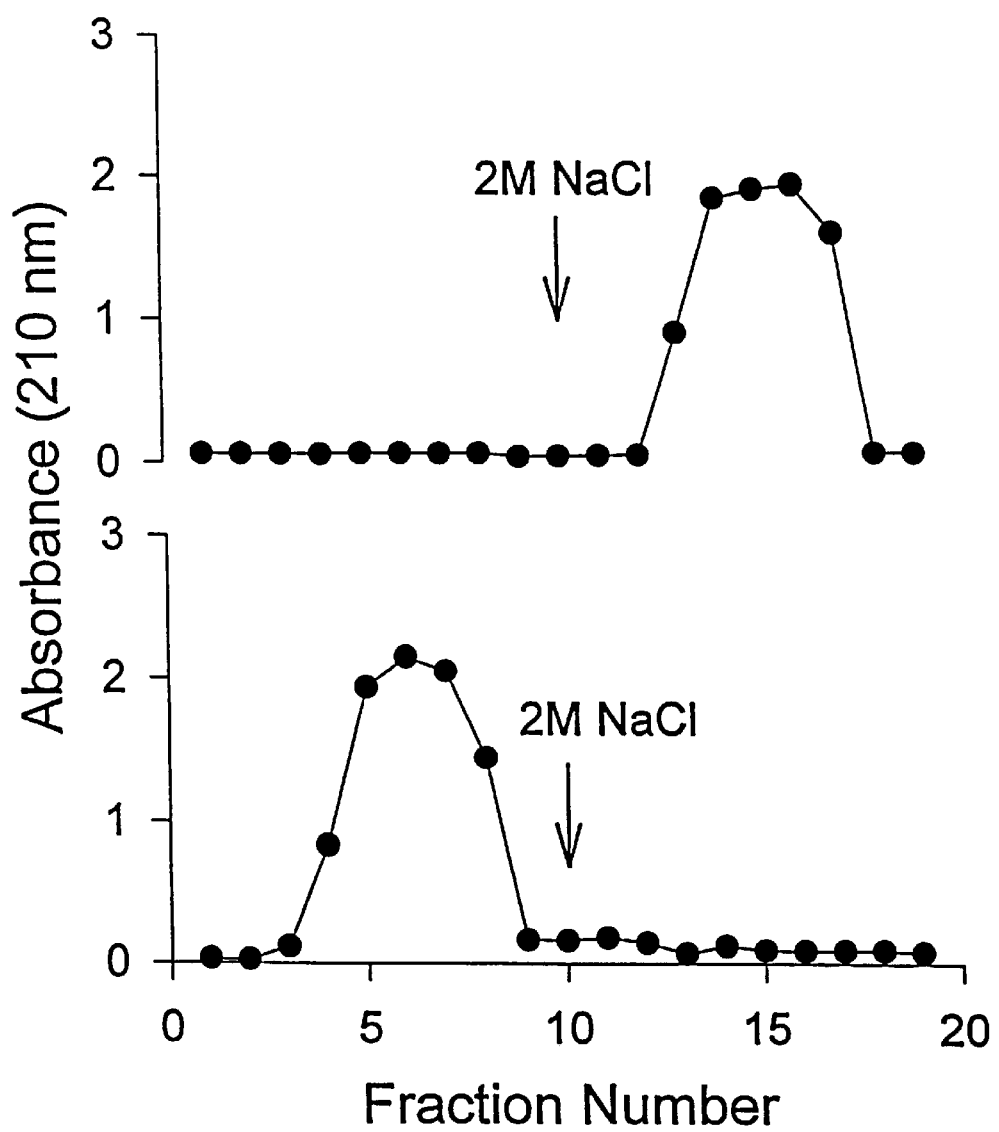

In the second experiment, N-acetylation of the polycation peptides was performed through a peracetylation reaction. Both PLA and PLL were dissolved in water to a concentration of $10^{-4}$ M and then the solutions were neutralized to a pH of 7.0 with sodium acetate. Five μl of acetic anhydride was added to 100 μl of this solution, followed by immediate vortexing, and the resulting solution was incubated for 10 min at room temperature. After repeating the procedures five times, the reaction mixtures were heated at 100° C. for 2 min and were then cooled on ice. For purification of N-acetyl polycationic peptides, 200 μl of the reaction mixtures were applied to CM Sepharose CL-6B cation-exchange columns (Pharmacia, Upsaala, Sweden, 0.7×5 cm) pre-equilibrated with 0.05 M phosphate buffer with a pH of 7.2. The polycationic peptides were first eluted from the column with the phosphate buffer, and then with a 2 M NaCl solution. Fractions of 320 μl were collected. The absorbance of each fraction was measured at 210 nm using a UV spectrophotometer. As shown in FIG. 4, unacetylated PLA eluted from the column after the addition of salt (Fractions 13–17) (Panel A), whereas acetylated PLA was completely eluted from the column before the salt solution was applied (Fractions 3–8) (Panel B). The same chromatographic pattern was obtained with PLL. The size of the peak for acetylated PLA (Fractions 3–8) was virtually identical to that of the peak for the original (unacetylated) PLA (Fractions 13–17), indicating the complete N-acetylation of PLA. Peak fractions for both the acetylated and unacetylated forms of the polycationic polypeptides were separately pooled and then dialyzed against PBS. The resultant polypeptides were tested for their effect on mucin release from HTSE cells.

Figure 5:
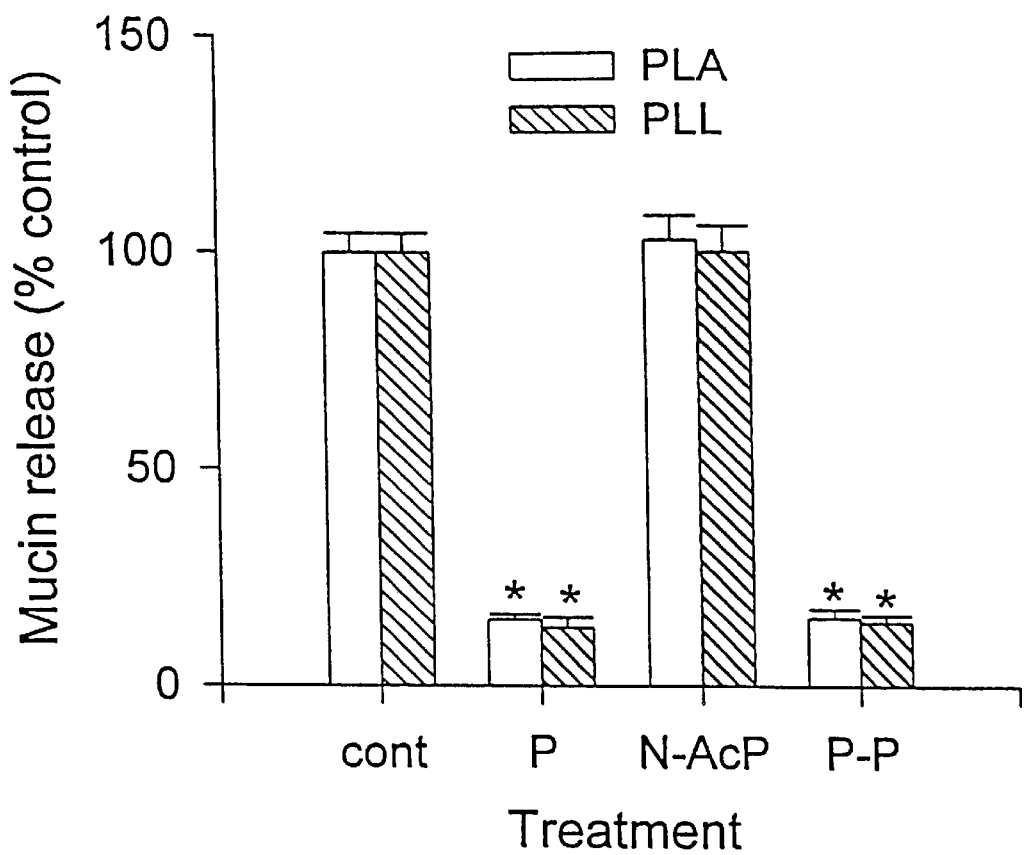

The "inhibitory" effect of $10^{-5}$ M of PLA or $10^{-5}$ M PLL was completely abolished following N-acetylation of these polycationic peptides (FIG. 5). There was no significant difference between the effect of the PLA or PLL that had not been column purified or the effect of column-purified PLA or PLL, indicating that the inhibitory effect of PLA and PLL was not due to contaminants in the preparation. The purity of the original preparation was also apparent based on the profile of the cation-exchange column chromatography (FIG. 4).

Example 4
Inhibition of ATP-Induced Mucin Release by PLA or PLL.

The effect of polycationic peptides on "stimulated" or "regulated" mucin release was also examined using ATP, which has previously been identified as a potent mucin-secretagogue for airway goblet cell mucins; Kim et al., 1991, Br. J. Pharmacol., 103:1053–1056. The ATP was prepared as a solution in PBS, with a final pH of between 7.0 and 7.4. ATP was added to the cell culture medium, both with and without polycationic peptides, during the 30 min chase period.

Figure 6:
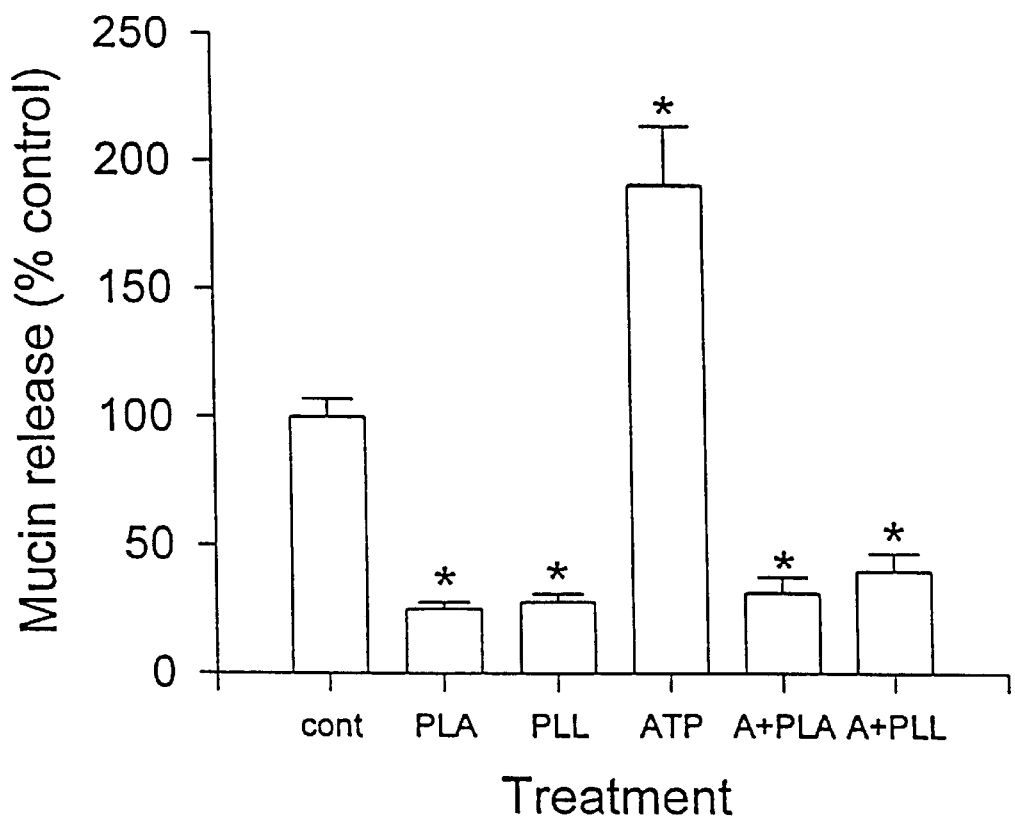

The stimulatory effect of ATP was completely blocked in the presence of either $10^{-5}$ M PLA or $10^{-5}$ M PLL, as shown in FIG. 6. The polycationic peptides not only blocked the ATP induced production of mucins, but also inhibited mucin production in the ATP treated cells to levels that were almost comparable to levels seen in non-stimulated cells treated with polycationic peptides. Therefore, a "super" inhibition of mucin was achieved in the ATP treated cells.

Example 5
Effects of High Molecular Weight PLL or PLA on Mucin Secretion.

High molecular weight PLL (average MW 78,000; ~533.5 residues) or PLA (average MW 92,000; ~528 residues) were also evaluated for activity in inhibiting mucin secretion from HTSE cells and for toxicity, using techniques described in examples 1–4 above. High molecular weight PLL and PLA inhibited mucin secretion in a dose-dependent fashion. However, the use of high molecular weight PLL and PLA was associated with cytotoxicity, as determined by LDH release assays.

Example 6
Effects of Low Molecular Weight PLL or PLA on Mucin Secretion.

Figure 7:
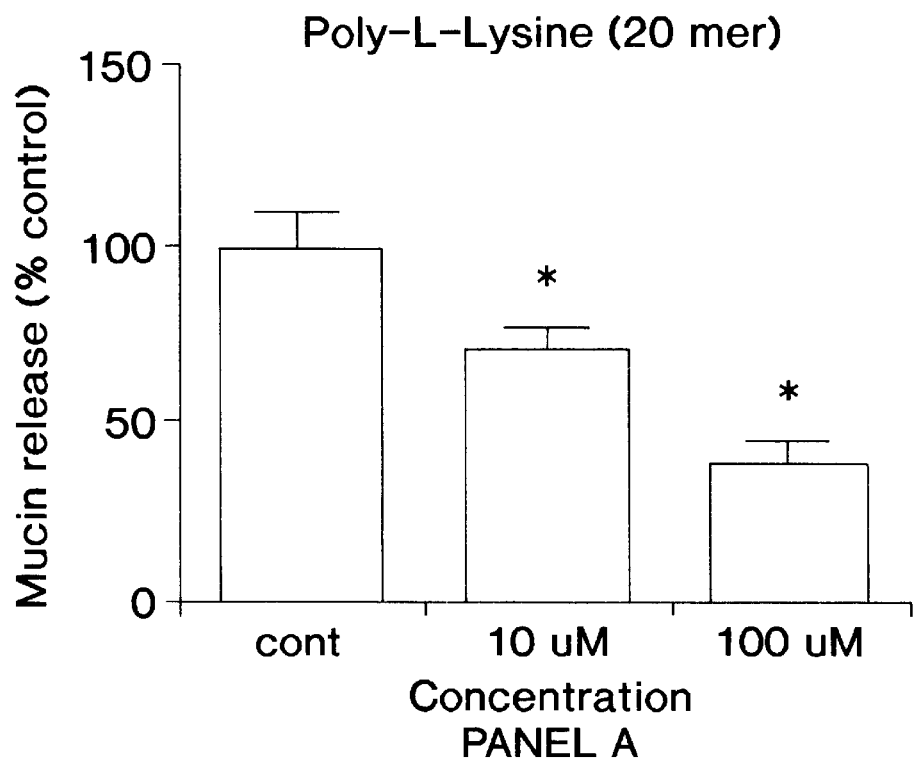
FIG. 7 is a bar graph showing the effects of low molecular weight PLL (20-mer) on mucin release in HTSE cells (Panel A) and on LDH release in HTSE cells (Panel B). An asterisk (*) indicates a value that is significantly different ($p<0.05$) from the control value based on the Student's t-test for unpaired samples.
Figure 7:
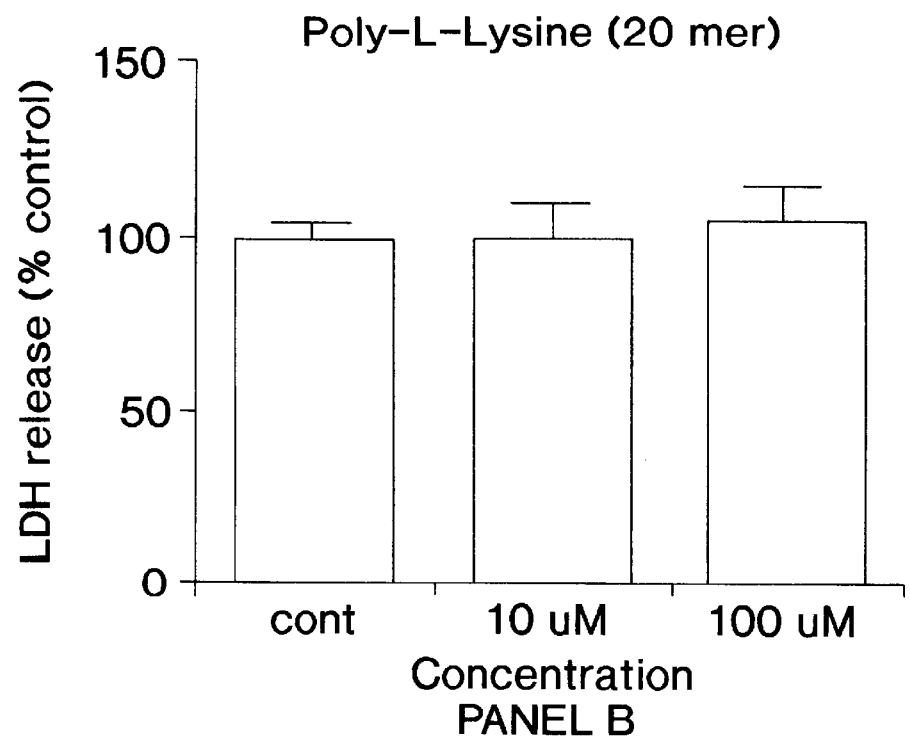
Figure 8:
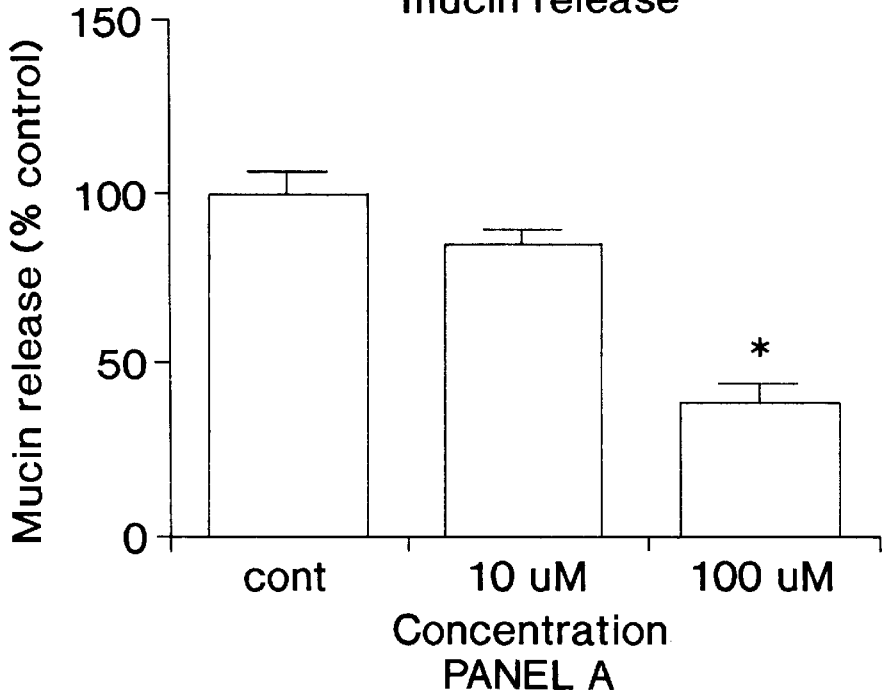
FIG. 8 is a bar graph showing the effects of low molecular weight PLA (20-mer) on mucin release in HTSE cells (Panel A) and on LDH release in HTSE cells (Panel B). An asterisk (*) indicates a value that is significantly different ($p<0.05$) from the control value based on the Student's t-test for unpaired samples.
Figure 8:
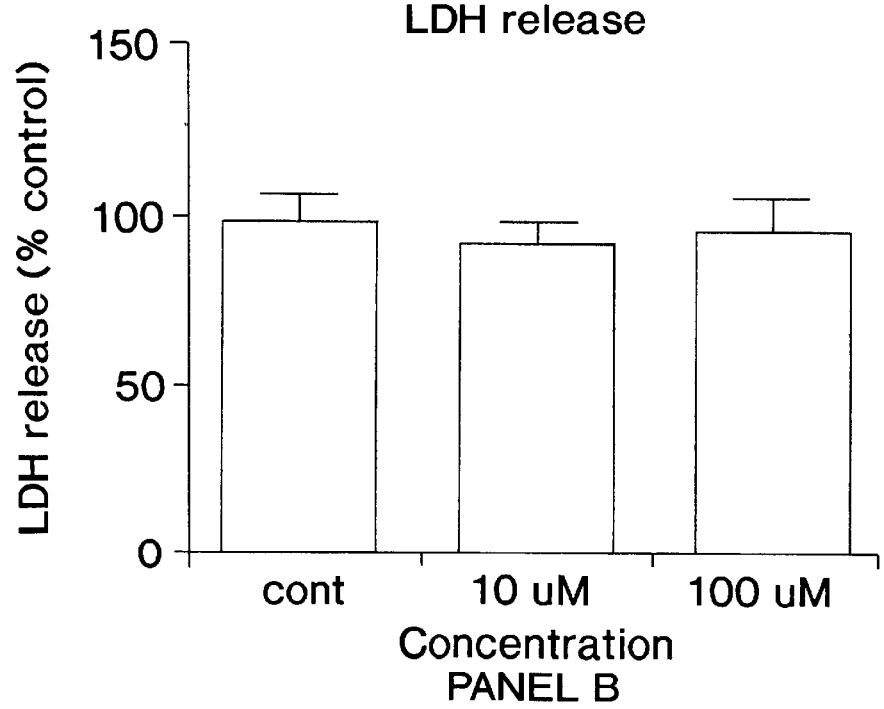
Figure 9:
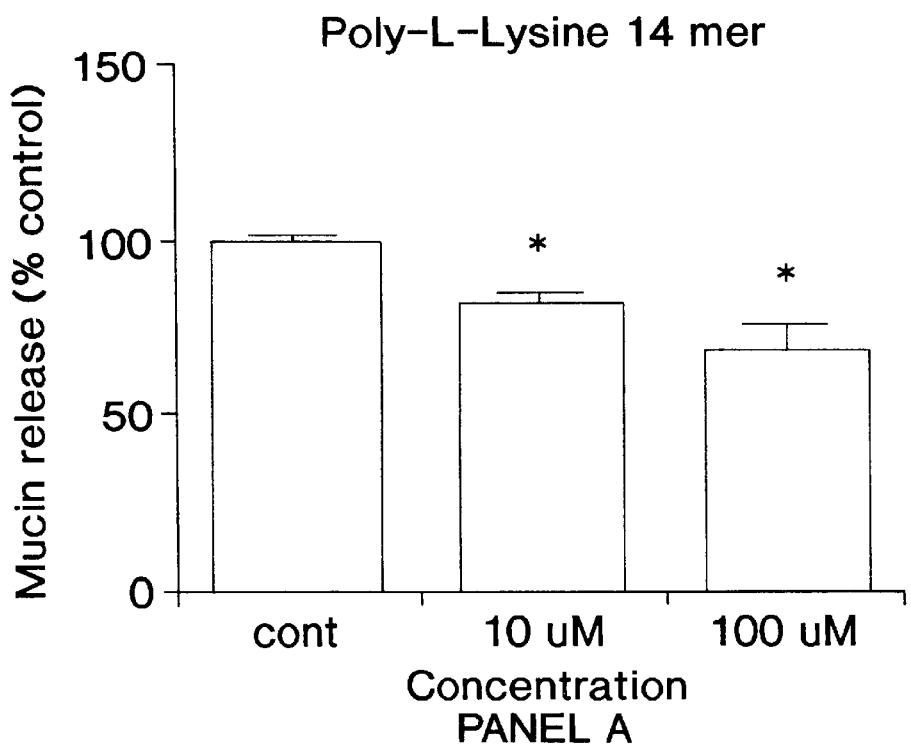
FIG. 9 is a bar graph showing the effects of low molecular weight PLL (14-mer) on mucin release in HTSE cells (Panel A) and on LDH release in HTSE cells (Panel B). An asterisk (*) indicates a value that is significantly different ($p<0.05$) from the control value based on the Student's t-test for unpaired samples.
Figure 9:
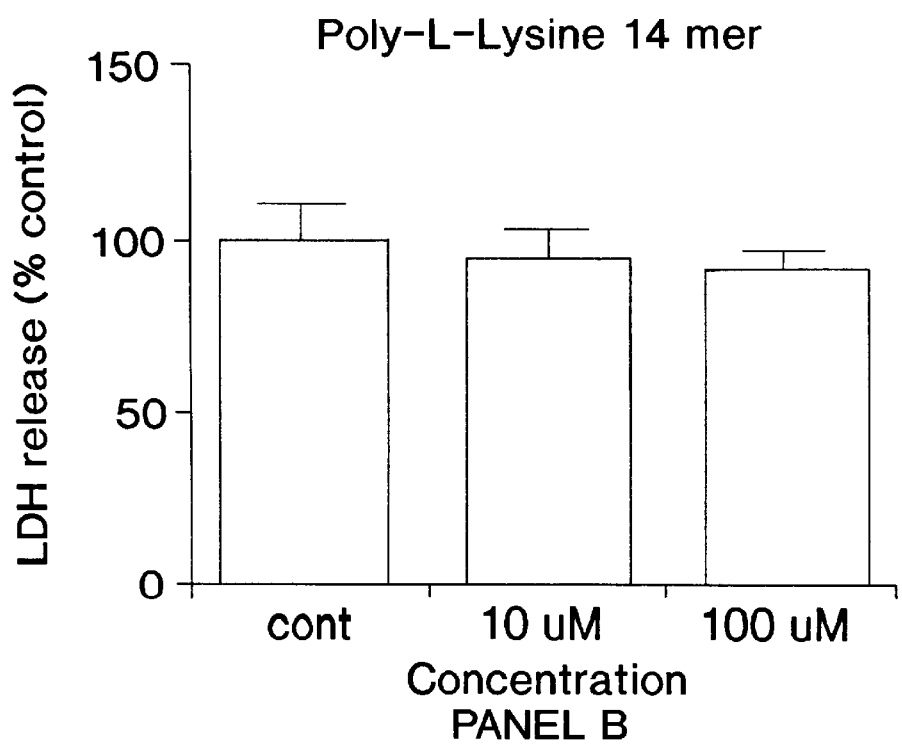
Figure 10:
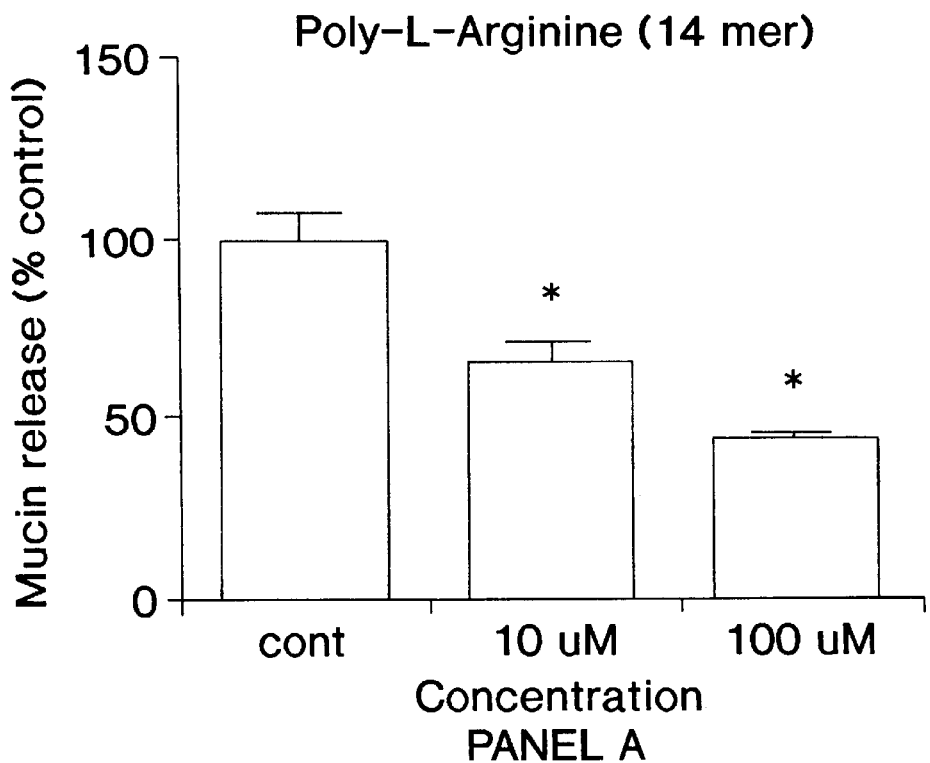
FIG. 10 is a bar graph showing the effects of low molecular weight PLA (14-mer) on mucin release in HTSE cells (Panel A) and on LDH release in HTSE cells (Panel B). An asterisk (*) indicates a value that is significantly different ($p<0.05$) from the control value based on the Student's t-test for unpaired samples.
Figure 10:
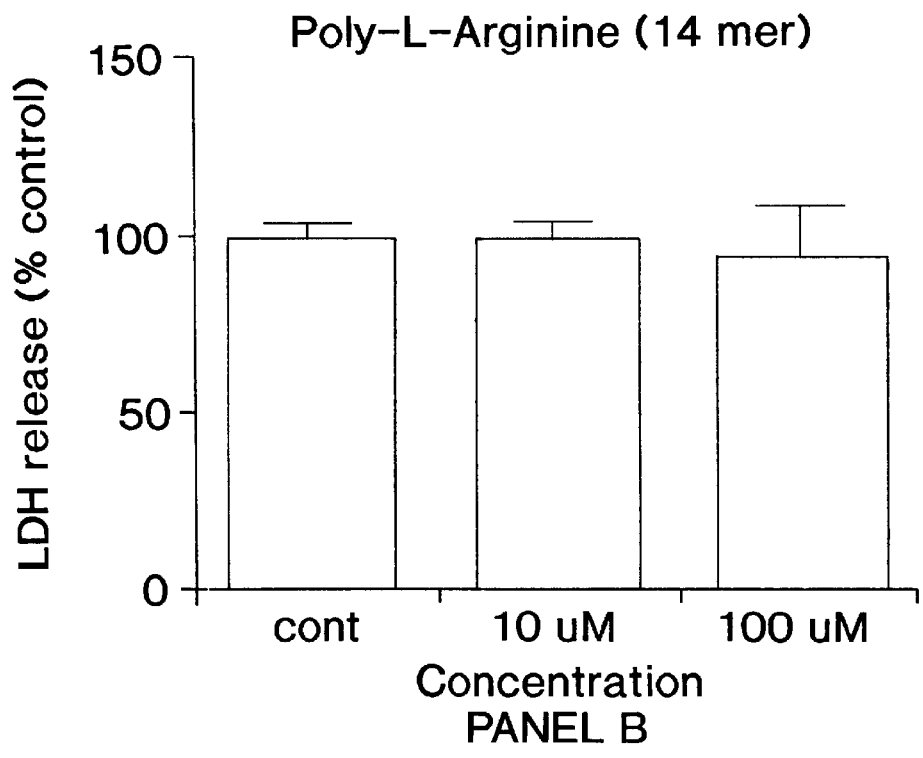
Figure 11:
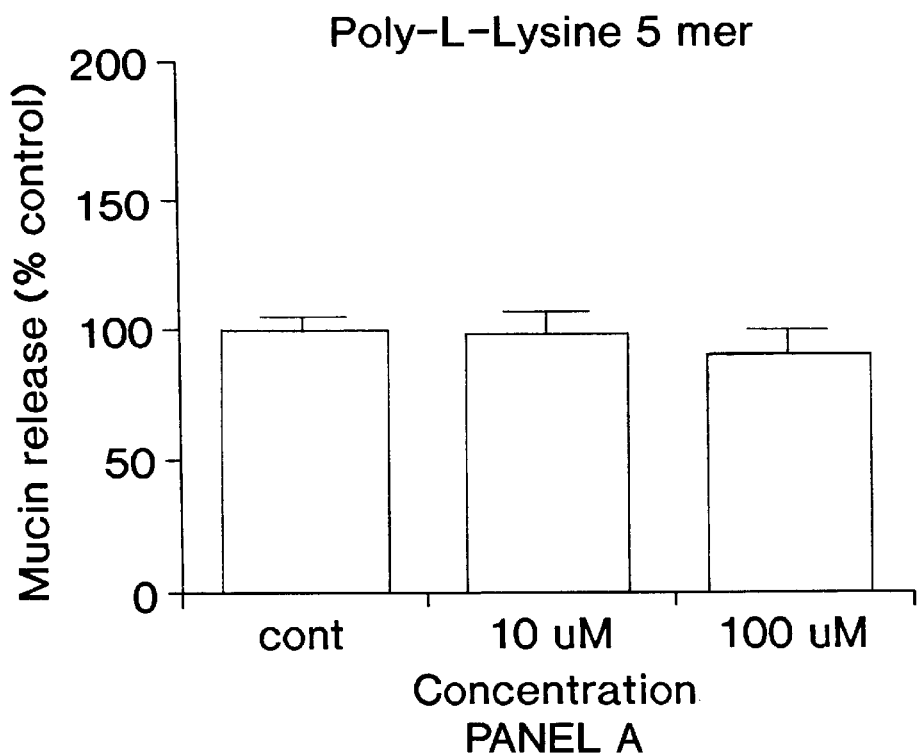
FIG. 11 is a bar graph showing the effects of low molecular weight PLL (5-mer) on mucin release in HTSE cells (Panel A) and on LDH release in HTSE cells (Panel B).
Figure 11:
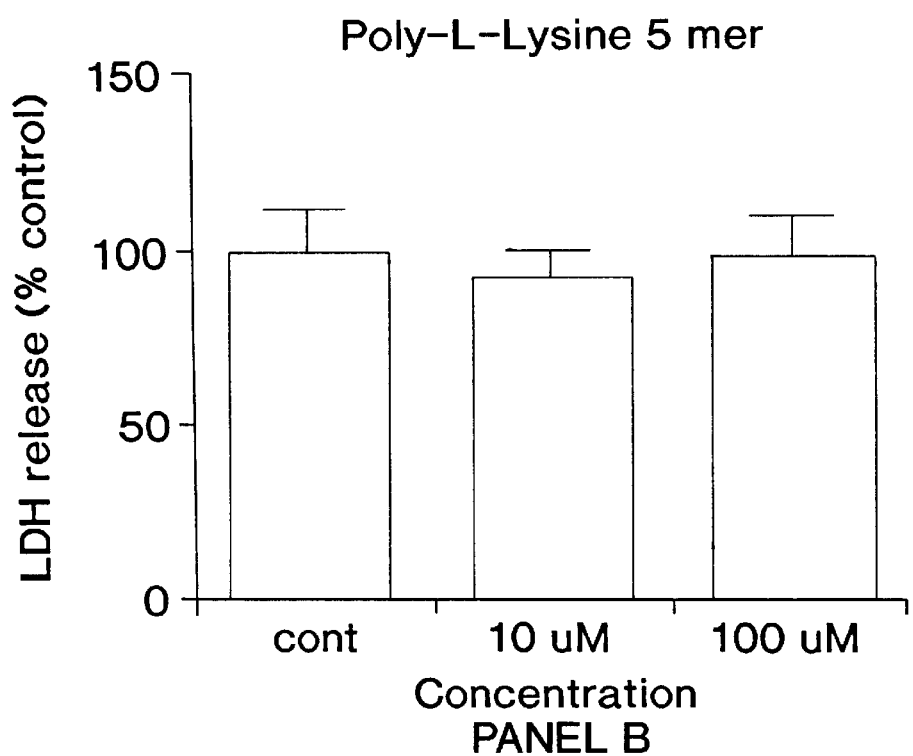
Figure 12:
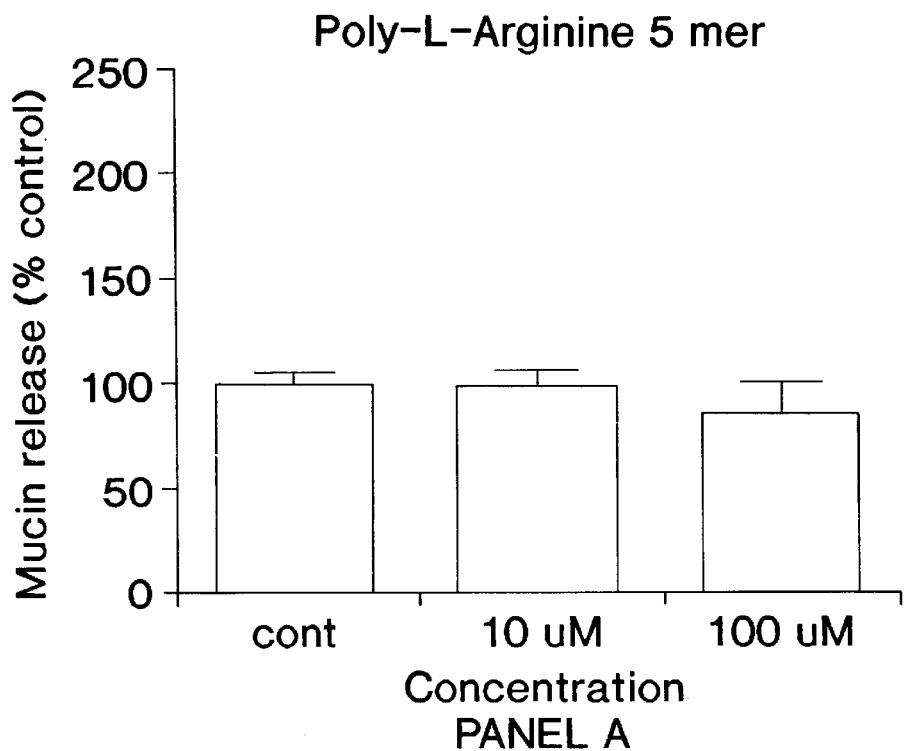
FIG. 12 is a bar graph showing the effects of low molecular weight PLA (5-mer) on mucin release in HTSE cells (Panel A) and on LDH release in HTSE cells (Panel B).
Figure 12:
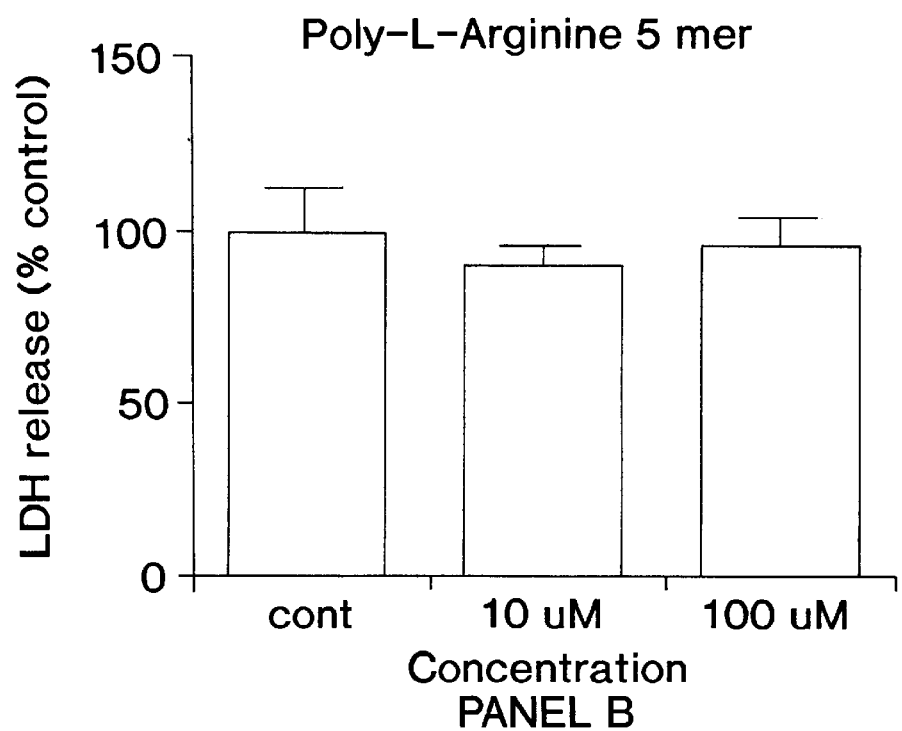

Low molecular weight PLL or PLA were also evaluated for activity in inhibiting mucin secretion from HTSE cells and for toxicity, using techniques described in examples 1–4 above. Low molecular weight PLL (20 residues) inhibited mucin secretion in a dose dependent fashion, without any evidence of cytotoxicity (FIG. 7). Low molecular weight PLA (20 residues) inhibited mucin secretion in a dose dependent fashion, without any evidence of cytotoxicity (FIG. 8). Low molecular weight PLL (14 residues) inhibited mucin secretion in a dose dependent fashion, without any evidence of cytotoxicity (FIG. 9). Low molecular weight PLA (14 residues) inhibited mucin secretion in a dose dependent fashion, without any evidence of cytotoxicity (FIG. 10). Low molecular weight PLL (5 residues) and PLA (5 residues) did not show any significant inhibition of mucin secretion (FIGS. 11 and 12).

Example 7
Effects of Inhaled PLL or PLA on $SO_2$-Induced Goblet Cell Metaplasia in Rats.

To examine the effects of PLL or PLA in vivo, the effect of PLL or PLA on goblet cell metaplasia in rats was determined. Exposure of rats to $SO_2$ was carried out essentially according to the method described in Kase et al, 1982, Arzneim-Forsch Drug Research 32:368–373. Eight to ten week-old male Sprague-Dawley rats were placed in a polyacrylic chamber (100 cm×60 cm×25 cm) and exposed to $SO_2$ for three weeks, three hours per day, five days per week. The $SO_2$ gas was generated from a solution containing 10% (W/V) sodium metabisulfite by aerosolization using an ultrasonic humidifier (Samsung Electronic Co., Korea). Concentrations of the generated $SO_2$ gas were monitored before and after the exposure using a $SO_2$ detector kit (Gastec Co., Japan), which has a detection range from 20 to 3600 ppm of $SO_2$. The concentration of the $SO_2$ gas inside the chamber was maintained at 150 ppm during all of the exposure periods.

PLA (average MW 10,800) was prepared in phosphate buffered saline (PBS), pH 7.2, in various concentrations. Following treatment of the animals with $SO_2$ for 2 weeks, animals were treated with both $SO_2$ and PLA during a third week. A 100 $\mu$l aliquot of one of the PLA solutions was administered to each rat using an inhaler (PAPI master, Starnberg, Germany), once a day for five consecutive days, during the period immediately following the two week $SO_2$ treatment period. PLA was administered between the hours of 10 am to 11 am and $SO_2$ was administered during the hours of 1 pm to 4 pm. At the end of third week, the animals were sacrificed in a $CO_2$ chamber and the airway tissues were processed for the conventional PAS staining. The histological examinations of the tissue sections (5 $\mu$m thick) revealed that goblet cell metaplasia (an increase in the number of purplish epithelial cells) induced by $SO_2$ could be prevented by PLA in a dose-dependent fashion (FIG. 13).

The preceding examples can be repeated with similar success by substituting the generically or specifically described reactants and/or operating conditions of this invention for those used in the preceding examples.

Without further elaboration, it is believed that one skilled in the art can, using 25 the preceding description, utilize the present invention to its fullest extent. The preceding preferred specific embodiments are, therefore, to be construed as merely illustrative, and not limitative of the remainder of the disclosure.

The entire disclosure of all patent applications, patents, and publications cited herein are hereby incorporated by reference.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A method of reducing mucin production in the airways of an animal comprising administering an effective amount of at least one polycationic polypeptide to the airways of the animal, wherein the poly cationic polypeptide has 5 to 60 amino acids, and wherein at least 20% of the amino acids are positively charged.

2. A method according to claim 1, wherein at least one polycationic polypeptide is poly-L-arginine, poly-L-lysine, or a heteropolymer of lysine and arginine.

3. A method according to claim 1, wherein the animal is treated for mucin hypersecretion.

4. A method according to claim 1, wherein the animal is treated for asthma, chronic bronchitis, cystic fibrosis, bronchiectasis, or chronic obstructive pulmonary disease.

5. A method according to claim 1, wherein polycationic polypeptide is administered by inhalation.

6. A method according to claim 1, wherein at least 50% of the amino acids are lysine or arginine.

7. A method according to claim 6, wherein at least 70% of the amino acids are lysine or arginine.

8. A method according to claim 7, wherein at least 90% of the amino acids are lysine or arginine.

9. A composition comprising at least one polycationic polypeptide and at least one inhalation adjuvant, wherein the polycationic polypeptide is polymerized through the alpha-amino group, and wherein the polycationic polypeptide comprises greater than 40% positively charged amino acids.

10. A composition comprising at least one polycationic polypeptide and at least one inhalation adjuvant, wherein the inhalation adjuvant is a propellant that is a compressed gas propellant or a liquefied gas propellant;

wherein the polycationic polypeptide is polymerized through the alpha-amino group, and wherein the polycationic polypeptide comprises greater than 20% positively charged amino acids.

11. A composition according to claim 10, wherein at least one polycationic polypeptide is poly-L-arginine, poly-L-lysine, or a heteropolymer of lysine and arginine.

12. A composition according to claim 10, wherein the polycationic polypeptide is a polypeptide having 5 to 60 amino acids, wherein at least 50% of the amino acids are lysine or arginine.

13. A composition according to claim 12, wherein at least 70% of the amino acids are lysine or arginine.

14. A composition according to claim 13, wherein at least 90% of the amino acids are lysine or arginine.

15. A device for administering a polycationic polypeptide to the airways of an animal comprising an inhalator containing a polycationic polypeptide, wherein the polycationic polypeptide is polymerized through the alpha-amino groups, wherein the polycationic polypeptide is contained within a pressurized pack, and wherein the polycationic polypeptide comprises greater than 20% posotively charged amino acids.

16. A device for administering a polycationic polypeptide to the airways of an animal comprising an inhalator containing a composition according to claim 10.

17. A device for administering a polycationic polypeptide to the airways of an animal comprising a pressurized pack containing a composition according to claim 12.

18. A device for administering a polycationic polypeptide to the airways of an animal comprising a pressurized pack containing a composition according to claim 13.

19. A method of reducing mucin production in the airways of an animal comprising administering effective amounts of a composition consisting essentially of at least one polycationic polypeptide and at least one inhalation adjuvant to the airways of the animal, wherein at least 20% of the amino acids of the polycationic polypeptide are positively charged.

20. A method of reducing mucin production in the airways of an animal, comprising administering to the airways of the animal an effective amount of at least one polycationic polypeptide, which is poly-L-lysine, or a heteropolymer of lysine and arginine.

21. A method of reducing mucin production in the airways of an animal, comprising administering to the airways of the animal an effective amount of a composition comprising at least one polycationic polypeptide essentially free of ingredients which neutralize or block the positive charges of the polypeptide to an extent that said mucin production is reduced, wherein at least 20% of the amino acids of the polycationic polypeptide are positively charged.

22. The method of claim 19, wherein the composition consists of at least one polycationic polypeptide, wherein at least 20% of the amino acids of the polycationic polypeptide are positively charged, and at least one inhalation adjuvant.

* * * * *